United States Patent [19]
Melendez et al.

[11] Patent Number: 5,912,456
[45] Date of Patent: Jun. 15, 1999

[54] INTEGRALLY FORMED SURFACE PLASMON RESONANCE SENSOR

[75] Inventors: Jose L. Melendez, Plano; Richard A. Carr, Rowlett; Robert C. Keller, Plano, all of Tex.

[73] Assignee: Texas Instruments Incorporated, Dallas, Tex.

[21] Appl. No.: 08/820,621

[22] Filed: Mar. 19, 1997

Related U.S. Application Data

[XX .
[60] Provisional application No. 60/013,665, Mar. 19, 1996.

[51] Int. Cl.$^6$ ...................................................... H01J 3/14
[52] U.S. Cl. ........................ 250/216; 250/225; 250/239; 356/369
[58] Field of Search .................................. 250/216, 225, 250/239, 208.1, 214; 356/369; 359/858, 859, 834

[56] References Cited

U.S. PATENT DOCUMENTS

| | | | |
|---|---|---|---|
| 4,844,613 | 7/1989 | Batchelder et al. | 356/318 |
| 4,889,427 | 12/1989 | Van Veen et al. | 356/445 |
| 4,931,384 | 6/1990 | Layton et al. | 435/7 |
| 5,322,798 | 6/1994 | Sadowski | 436/113 |
| 5,341,215 | 8/1994 | Seher | 356/445 |
| 5,351,127 | 9/1994 | King et al. | 356/445 |
| 5,374,563 | 12/1994 | Maule | 436/165 |
| 5,396,061 | 3/1995 | Taniguchi et al. | 250/216 |
| 5,661,297 | 8/1997 | Aleshire et al. | 250/239 |
| 5,689,108 | 11/1997 | Ohyama | 250/239 |

FOREIGN PATENT DOCUMENTS

| | | |
|---|---|---|
| 0 341 927 A1 | 11/1989 | European Pat. Off. . |
| 0 516 481 A2 | 12/1992 | European Pat. Off. . |
| 0 517 930 A1 | 12/1992 | European Pat. Off. . |
| 06 058873 A | 3/1994 | Japan . |
| 06 167443 A | 6/1994 | Japan . |

OTHER PUBLICATIONS

Melendez, Jose, et al., "A Commercial Solution for Surface Plasmon Sensing", Sixth International Meeting on Chemical Sensors, Gaithersburg, MD, USA, 22–25 Jul. 1996; Sensors and Actuators B (Chemical), vol. B35, No. 1–3, ISSN 0925–4005, Elsevier, Switzerland, Sep. 1996, pp. 212–216.

Kondyrev, Alexandre M., et al., "Moldable Optical Element: A New Tool to Obtain the Infrared Attenuated–Total–Reflection Spectrum of a Rough Surface", Applied Optics, 1 Aug. 1995, USA, vol. 34, No. 22, ISSN 0003–6935, pp. 4989–4992.

*Primary Examiner*—Que T. Le
*Attorney, Agent, or Firm*—David Denker; Robby T. Holland; Richard L. Donaldson

[57] ABSTRACT

A surface plasmon resonance sensor includes a light source 10 and a polarizer 18 for producing polarized light which passes through a transparent body 12 and strikes a thin conductive film 26 disposed on the exterior surface of the body 12. The film 26 exhibits surface plasmon resonance when the light strikes the film at a "resonance angle". By determining the angle at which surface plasmon resonance occurs, the refractive index of the material on the side of the film 26 opposite to the side which reflects the polarized light can be measured.

24 Claims, 2 Drawing Sheets

INTEGRALLY FORMED SURFACE PLASMON RESONANCE SENSOR

This application claims benefit of Provisional Application 60/013,665 filed Mar. 19, 1996.

FIELD OF THE INVENTION

This invention relates broadly to the field of optical sensors and, more particularly to the field of sensors used in the fields of chemical, biochemical, biological or biomedical analysis, process control, pollution detection and control, and other similar areas.

BACKGROUND OF THE INVENTION

Surface plasmon resonance is an optical surface phenomenon that has been employed in sensors used in the fields of chemical, biochemical, biological or biomedical analysis. A surface plasmon is a surface charge density wave at the surface of a thin conducting film. A description of this phenomenon is found in the article by H. Raether in Physics Thin Films, 1977, 74 pp 237–244. This resonance can be observed when a polarized beam of monochromatic light is totally internally reflected from a dielectric interface having a thin conducting film formed thereon. Usually the interface comprises a smooth surface of a transparent body such as glass. The light internally reflected by the interface has a minimum intensity at a particular angle referred to as a resonant angle in the literature. This angle is determined by the dielectric conditions adjacent the metal film and the properties of the film itself.

In prior sensors utilizing surface plasmon resonance, a thin metal film is usually applied to a flat surface of a glass prism. The resonance angle is determined by directing a polarized light beam through the prism onto the surface with the metal film thereon and measuring the intensity of the light reflected therefrom and through an external surface of the prism. Such arrangements, however, require a very high degree of precision in order to manufacture and align the separate optical parts so as to be able to produce accurate measurements.

The basis for the use of surface plasmon resonance for sensing is the fact that the oscillation of a surface-plasma of free electrons which exists at a conductor-dielectric boundary is affected by the refractive index of the material adjacent the conductor film surface on the side thereof opposite the prism. For a given wavelength of radiation, the resonance occurs when the angle of incidence of the polarized radiation has a particular value and this value is dependent on the refractive index of the material adjacent the film. As such, changes in the refractive index give rise to changes in the angle at which surface plasmon resonance occurs. When polarized light strikes the thin metal film at the "resonance angel", the intensity of the reflected light therefrom is minimized. Hence, by detecting the angle at which this minimum occurs, the refractive index of the material adjacent the film can be determined. The usefulness of this approach, however, has been limited due to system complexity related primarily to mechanical alignment issues.

SUMMARY OF THE INVENTION

The problems associated with earlier sensors are overcome by the present invention which includes an integral structure having a portion of the detector system disposed inside the sensor housing. The housing is made of a material which is transparent to the radiation produced by a radiation source. A radiation source produces light that passes through the housing and strikes an exterior surface of the housing on which a thin conducting layer is formed. The light reflected from the conducting layer is directed toward an array of radiation detectors. The detector having the minimum output level is associated with radiation rays from the source that have bounced off the thin conducting layer at the "resonance" angle which is a function of the refractive index of the material contacting the conducting layer.

BRIEF DESCRIPTION OF THE DRAWINGS

The above mentioned objects, advantages and features of this invention are described below in connection with the drawings wherein.

DETAILED DESCRIPTION

Figure 1:
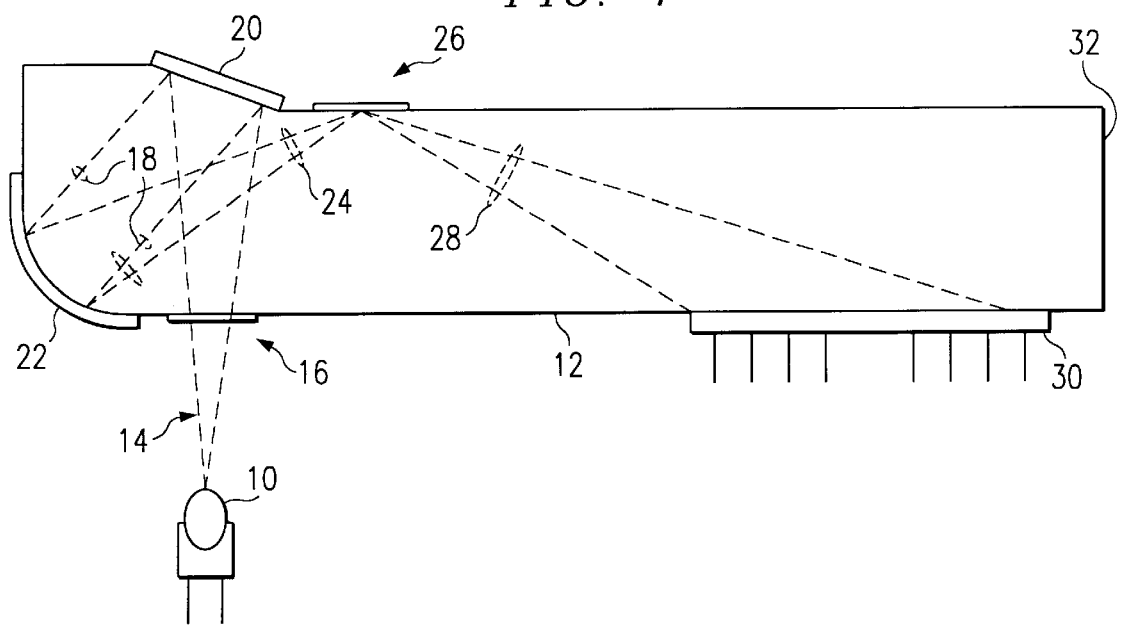
FIG. 1 illustrates one embodiment of the present invention wherein polarized light rays are converging toward each other prior to contacting a surface plasmon resonance layer.

FIG. 1 illustrates one embodiment of the present invention. In this configuration, a radiation source 10, which may comprise a light emitting diode (LED), a laser diode or any other suitable source of radiation, is disposed external to a housing 12 and is positioned to direct radiation (light rays) 14 in a direction toward the housing 12. The housing 12 is made of a material which is transparent to the radiation from the source 10 such as suitable plastics or epoxy. In particular, a plastic marketed under the trademark Ultem by General Electric has been found useful especially for radiation sources in the infrared range. Other usable materials include polymethylmethacrylate or polycarbonate.

A polarizing filter 16 is disposed between the radiation source 10 and the housing 12 to produce polarized radiation 18 which enters the housing 12. There are many suitable polarizers such as the plastic polarizing material sold by Polaroid Corporation known as HN7 Linear Polarizer. By reason of the fact that the radiation source 10 acts somewhat like a point source of radiation, the radiation rays (light rays) diverge from each other. Likewise, the polarized radiation 18 consists of rays which are diverging from each other as well.

The diverging polarized radiation 18 passes through the surface of the housing 12 and reflects from a planar mirror 20 which is disposed so that the plane thereof is not normal to the direction to the polarized radiation 18. The diverging polarized radiation 18, after being reflected from the mirror 20, is directed toward a curved (concave) mirror 22 disposed on a curved exterior surface of the housing 12. When the mirror 22 is concave, the shape of this mirror can be constructed so that the radiation reflecting therefrom is converging as illustrated at 24. By altering the curve of the mirror 22, it is also possible for the radiation rays at 24 to be substantially parallel or even diverging. The advantage of utilizing converging radiation, however, is that the reflected polarized radiation can be directed (focused) onto a smaller surface plasmon resonance (SPR) layer 26 than would occur for the same general configuration where the radiation is diverging just prior to striking the SPR layer 26.

The surface plasmon resonance layer 26 comprises a thin layer of a conductive material such as copper, silver or gold having a substantially uniform thickness. The layer 26 is preferably planar although other configurations, such as convex or concave configurations, or featured with steps, periodic or non-periodic, can also be utilized. This layer 26, in one embodiment of the invention, comprises a film of gold approximately 275 angstroms thick. The thickness of a surface plasmon resonance layer may vary from about 200 to about 600 angstroms and still permit surface plasmon resonance to occur. The specific film thickness is determined by experimentation with respect to the frequency of the radiation for the source 10 and the properties of the conductive material used for layer 26. As is known in the art, when radiation strikes a thin conductive film at the interface of an insulator, the intensity of reflection therefrom is a function of the angle of incidence of the radiation onto the film and the refractive index of the material in contact with the other side of the film. Hence, by determining the angle at which minimum reflectance occurs, it is possible to determine the index of refraction of the material on the side of the film opposite the side the radiation is reflected from.

In accordance with utilizing the principal of operation described above, the configuration of FIG. 1 produces diverging radiation 28 which is reflected from the thin surface plasmon resonance layer 26. The diverging radiation 28 passes through the housing 12 and is intercepted by a detector array 30 disposed at or near an external surface of the housing 12. For optical radiation, the detector array 30 comprises an array of photodetectors. Each detector in the array 30 produces a signal on an output pin with a voltage that is proportional to the intensity of the radiation striking the detector. By measuring the voltage at each detector and knowing the angle that the radiation striking that detector intercepted the surface plasmon resonance layer, one can produce a plot of reflected radiation intensity as a function of the angle. That plot can be correlated to the index of refraction of the substance on the side of the surface plasmon resonance layer opposite the side which reflects the radiation.

Those of skill in the art will recognize that the physical location of the elements illustrated in FIG. 1 can be moved or relocated while retaining the function described above. For example, the light source 10 and the polarizer 16 could have been located within housing 12. Such a placement would have the advantage of permitting the source 10 to be fixedly located with respect to other elements thereby eliminating one of the complicating factors associated with prior art devices using surface plasmon resonance. In addition, the location and shape of the mirrors utilized for reflecting the radiation could take on other configurations and locations so long as polarized radiation strikes a surface plasmon resonance layer and the intensity of the radiation reflected therefrom is measured as a function of the angle of the radiation striking the surface plasmon resonance layer.

A further modification is to include a filter 32 to filter out radiation at frequencies other than at frequencies produced by the source 10. As illustrated in FIG. 1, the filter 32 overlies the detector 30 and serves to pass radiation at the frequencies produced by the source to the detector 30. As such, the filter 32 serves to make the sensor of the invention less susceptible to noise caused by other radiation sources. One suitable filter is the plastic filter material marketed by Polaroid Corporation and known as XR-84. This material is especially suitable for passing infrared radiation and blocking visible radiation.

An alternative to utilizing a filter 32 is to utilize a plastic or epoxy material for the housing 12 which is transparent to frequencies produced by the source 10 and opaque to frequencies outside the desired frequency range of interest for a given sensor.

Figure 2:
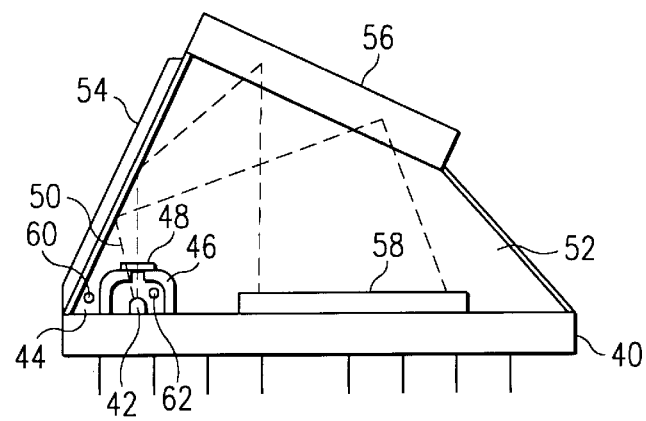
FIG. 2 illustrates one embodiment of the present invention wherein polarized light rays are diverging from each other prior to contacting a surface plasmon resonance layer.

FIG. 2 illustrates an alternative configuration to that illustrated in FIG. 1. This alternative configuration includes a substrate 40 on which the sensor is constructed. A light source 42 is preferably located above the substrate 40 although it could be disposed in the substrate 40 itself. Disposed above the light source 42 is a physical aperture 44 in a light shield 46 through which light from the source 42 passes. A polarizer 48 is located near the aperture 44 to polarize the light passing through the aperture 44. The polarized light 50 continues through the housing 52 and strikes a thin surface plasmon resonance layer 54. The polarized light is reflected internally from the layer 54 and continues through the housing 52 and strikes a planar mirror 56. The polarized light reflects from the mirror 56 and is directed through the housing 52 and onto a detector array 58.

The polarizer 48 does not need to be located closely adjacent the aperture 44 but may be disposed at any point along the radiation path between the source 42 and the detector array 58. This aspect of polarizer placement is true for all the alternative embodiments illustrated herein. It is also to be noted that all disclosed embodiments of the present invention will function without a polarizer. The polarizer serves to enhance the operation of the detector of the present invention but is not a requirement for its operation.

As can be readily discerned from FIG. 2, the light source 42, the light shield 46 with aperture 44 therethrough, the polarizer 48 and the detector array 58 are disposed within the housing 52. As with the housing 12 described above, the housing 52 is made of a material which is transparent or substantially transparent to the light from the light source 42. Because the housing 52 is formed around other elements, somewhat different materials than those used for making the device of FIG. 1 are preferable to prevent damage to those elements being encapsulated. In particular, an epoxy marketed under the trademark Epocast® 2013 Parts A/B by Furane Products Company has been found useful especially for radiation sources in the infrared range. Other usable materials include Emerson & Cumming, Stycast 1269A Parts A/B, Tracon Trabond F114, Dexter Hysol OS1000, Norland 61 and 63, Dexter Hysol MG18 or Nitto 8510-1100.

The housing 52 is formed in a shape so that light from the source 42 will reflect from the SPR layer 54, the mirror 56 and strike the detector array 58. Any configuration accomplishing this is suitable. However, there are several considerations that need to be taken into account in designing sensors of the type illustrated in FIG. 2. In the first place, it is desirable to have the radiation impinging on the detector array 58 at angles as close as possible to 90 degrees. This is due to the fact that the sensitivity of the discrete detector elements used in the detector array 58 are most sensitive to light impinging thereon along an optical axis thereof. Light impinging thereon from angles where the light rays are not parallel to the optical axis results in a lower output signal. By designing the structure of FIG. 2 to have the light strike the detector array 58 at an angle close to 90 degrees, the detector will have the maximum possible sensitivity. For most purposes, however, if the angle at which light strikes the detector array 58 is between about 60 and 90 degrees, the off axis falloff of each detector in the array 58 is not considered to be a major problem. Indeed, with calibration, the sensor of this invention can have light incidence angles of less than about 45 degrees and still be quite useful.

It is to be further noted from FIG. 2 that the surface plasmon resonance layer 54 is preferably formed on a surface of the exterior of the housing 52. It is also possible to have the surface plasmon resonance layer 54 (a thin conductive film) disposed on a glass slide or the like which is located adjacent an exterior surface of the housing 52 and having an index matching fluid disposed between the slide and the housing. It is also to be noted that the mirror 56 is preferably formed on an exterior surface of the housing 52. This mirror will have sufficient mass so that the effect of surface plasmon resonance will not occur on the surface thereof.

Further alternative designs are possible. For example, it is possible to utilize a surface plasmon resonance layer 54 disposed on a curved or featured exterior surface of the housing 52 (not illustrated). Likewise, the mirror 56 may be constructed on a curved surface. It is also possible to have more than one mirror and/or SPR surface disposed along the ray path between the source 42 and the detector array 58. It will also be clear that the radiation from the source 42 may strike a mirror prior to striking the surface plasmon resonance layer 54. Further variations in the radiation path and corresponding structure of the housing 52 may be conceived while retaining the functionality of the sensor illustrated herein.

The structure as illustrated in FIG. 2 does not have a filter 32 as illustrated for the sensor of FIG. 1. In this arrangement, if one wishes to eliminate the effect of stray radiation striking the detector array 58, a filter can be disposed between the detector array 58 and the mirror 56 (as illustrated in FIG. 1 for filter 32) and preferably placed adjacent the detector array 58. Alternatively, the housing 52 may be made of a material transparent to radiation at the frequencies produced by the source 42 and opaque to other frequencies. In either configuration, radiation at frequencies other than those produced by the source 42 will not form a significant portion of the output of the detector array 58.

The detector of FIG. 2 additionally includes a temperature sensor 60 disposed as close to the surface plasmon resonance (SPR) layer 54 and also to the surface of the housing 52 as is practical. This temperature sensor 60 produces an electrical signal indicative of the temperature of the SPR layer 54 during operation thereof. This temperature signal can be utilized to compensate for apparent changes in the measured index of refraction by the invention as a result of changes in the operating temperature of the device.

The detector of FIG. 2 additionally includes a reference detector 62 disposed within the light shield 46. This detector 62 is used to calibrate the invention over long periods of time since the intensity of a source 42 may vary over time.

Figure 3:
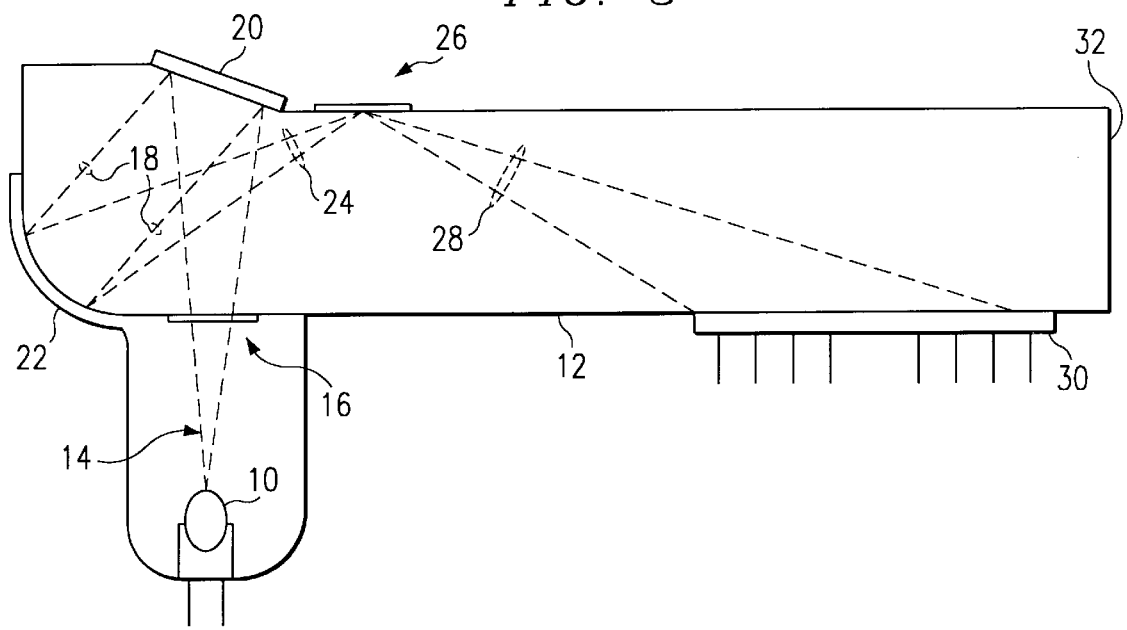
FIG. 3 illustrates an alternative configuration with the radiation source disposed within the detector housing.

FIG. 3 illustrates an alternative configuration to that illustrated in FIG. 1. The principal difference is that the radiation source 10 and polarizer 16 are encapsulated within the housing 12. In addition, due to the fact that the radiation source 10 is encapsulated, the materials suitable for the housing 12 of FIG. 3 are preferably those suitable for making the housing of FIG. 2.

The photodetector 30 of FIG. 3 is illustrated at a position closely adjacent to the housing 12. The term "closely adjacent" as used herein means that the photodetector 30 with an optional optical filter 32 thereon may be positioned within housing 12, in contact with an exterior surface of the housing 12 or spaced therefrom some distance as illustrated in FIG. 3. As it is important to prevent stray light to which the photodetector 30 is sensitive from being detected thereby, light baffles (not shown) or filters may be employed to prevent stray and undesired light from striking the photodetector 30.

Figure 4:
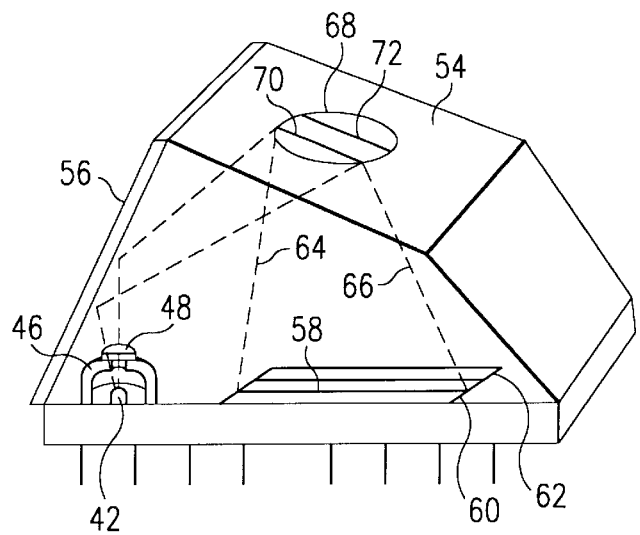
FIG. 4 illustrates another alternative configuration with two detector arrays disposed within the housing.

FIG. 4 illustrates yet another variation on the present invention. This configuration is similar to that illustrated in FIG. 2. In FIG. 4, however, the detector array 58 has two lines of detector elements 60 and 62. The first line of detector elements 60 is associated with the radiation path indicated by dotted lines 64 and 66. The radiation traversing the path from the source 42 to the detector array 58 reflects from the mirror 56 onto the SPR surface 54 in an area indicated by the ellipse 68. The radiation reflecting from the SPR surface 54 along line 70 will strike the first line of detector elements 60. The radiation reflecting from the SPR surface 54 along line 72 will contact the second line of detector elements 62. In this fashion two lines detectors can be utilized in this configuration. By utilizing a filter over each of the lines of detectors 60 and 62 having different filtering characteristics, it is possible to simultaneously test the index of refraction of the material contacting the SPR surface 54 with two different frequencies of radiation. It is also possible to test using different angles of radiation striking the SPR surface 54 by displacing the one of the lines of detectors 60 and 62 in the direction of these lines such that the angle of radiation reflecting from the SPR surface 54 and striking the displaced line of detectors is not the same as the angle of radiation reflected from the surface 54 and striking the other line of detectors.

The above description has been made with particular emphasis on the structure of the alternative embodiments illustrated in the attached drawings. It will be recognized by those of skill in the art, however, that the above mentioned and other modifications to the structure of the invention can be made without departing from the spirit and scope of the invention as defined in the following claims.

What is claimed is:

1. A surface plasmon sensor comprising, in combination:
   a source of electromagnetic radiation having a given frequency range;
   a housing transparent to said electromagnetic radiation in said frequency range;
   a thin surface plasmon resonance layer, the layer having a interior surface disposed on an exterior surface of said housing and an outer surface;
   an array of photodetectors disposed closely adjacent the surface of said housing and substantially coplanar with said source;
   said surface plasmon resonance layer and said photodetectors being disposed relative to each other so that said radiation from said source reflects off said interior surface and strikes at least some of said photodetectors, whereby said radiation's intensity varies as a function of which said photodetector is struck, said intensity variation function being affected by the index of refraction of a material that comes in contact with said outer surface.

2. The surface plasmon sensor of claim 1 additionally including a thermal sensor disposed in said housing providing a signal for calibrating said surface plasmon sensor.

3. The surface plasmon sensor of claim 1 additionally including a radiation sensor in said housing for sensing the intensity of said electromagnetic radiation for calibrating said surface plasmon sensor.

4. The surface plasmon sensor of claim 1 additionally including at least one mirrored surface disposed between said source of electromagnetic radiation and said photodetectors for modifying the direction of said radiation so that it strikes at least some of said photodetectors.

5. The surface plasmon sensor of claim 2 additionally including a radiation sensor in said housing for sensing the intensity of said electromagnetic radiation for calibrating said surface plasmon sensor.

6. The surface plasmon sensor of claim 1, wherein said source of electromagnetic radiation and said array of photodetectors are mounted upon a common substrate.

7. The surface plasmon sensor of claim 3 additionally including at least one mirrored surface disposed between said source of electromagnetic radiation and said photodetectors for modifying the direction of said radiation so that it strikes at least some of said photodetectors.

8. The surface plasmon sensor of claim 1, wherein said source of electromagnetic radiation is disposed within said housing.

9. The surface plasmon sensor of claim 1 wherein said radiation strikes said photodetectors at an angle between about 60 and 90 degrees.

10. The surface plasmon sensor of claim 4 wherein said radiation strikes said photodetectors at an angle between about 60 and 90 degrees.

11. The surface plasmon sensor of claim 1 additionally including a filter disposed in said housing to prevent radiation other than said radiation from said source from striking said photodetectors.

12. The surface plasmon sensor of claim 11 wherein said filter comprises the material of said housing which is substantially opaque for all radiation to which said photodetectors are sensitive other than said radiation from said source.

13. The surface plasmon sensor of claim 4 wherein each said mirrored surface is disposed on an exterior surface of said housing.

14. The surface plasmon sensor of claim 4 wherein at least one said reflective surface is formed on a curved surface.

15. The surface plasmon sensor of claim 1 wherein the rays of said radiation striking said surface plasmon resonance layer are diverging from each other.

16. The surface plasmon sensor of claim 1 wherein said rays of said radiation striking said surface plasmon resonance layer are converging toward each other.

17. The surface plasmon sensor of claim 1 wherein said rays of said radiation strike said surface plasmon resonance layer substantially parallel to each other.

18. The surface plasmon sensor of claim 1 additionally including a filter disposed adjacent said array of photodetectors for blocking radiation from striking said photodetectors having a frequency different from the frequency of said source of electromagnetic radiation.

19. The surface plasmon sensor of claim 1 additionally including a polarizing filter disposed in the path of said radiation between said source and said array of photodetectors.

20. The surface plasmon sensor of claim 1 wherein the surface on which said surface plasmon resonance layer is formed is a curved surface.

21. The surface plasmon sensor of claim 14 wherein the surface on which said surface plasmon resonance layer is formed is a curved surface.

22. A surface plasmon sensor comprising, in combination:

a source of electromagnetic radiation;

a housing surrounding said source of electromagnetic radiation and transparent to said electromagnetic radiation;

a polarizer disposed in said housing for producing polarized radiation from said electromagnetic radiation;

a thin surface plasmon resonance layer disposed on an exterior surface of said housing;

an array of photodetectors disposed in said housing and substantially coplanar with said source;

the polarized radiation from said polarizer, said surface plasmon resonance layer and said photodetectors being disposed relative to each other so that said polarized radiation reflects off said surface plasmon resonance layer and strikes at least some of said photodetectors.

23. A surface plasmon sensor comprising, in combination:

a housing transparent to electromagnetic radiation in a given frequency range;

a source of electromagnetic radiation in said given frequency range and disposed within said housing;

a polarizer for producing polarized radiation from said electromagnetic radiation and disposed within said housing;

a thin electrically conductive layer disposed on an exterior surface of said housing;

an array of photodetectors disposed closely adjacent the surface of said housing;

the polarized radiation from said polarizer, said electrically conductive layer and said photodetectors being disposed relative to each other so that said polarized radiation reflects off said electrically conductive layer and strikes at least some of said photodetectors.

24. The surface plasmon sensor of claim 23, wherein said thin electrically conductive layer is a surface plasmon resonance layer.

* * * * *